United States Patent
Kojima et al.

(10) Patent No.: US 7,019,183 B2
(45) Date of Patent: Mar. 28, 2006

(54) PROCESS FOR PRODUCING ADAMANTANE COMPOUND

(75) Inventors: Akio Kojima, Yamaguchi (JP); Kouichi Kodoi, Yamaguchi (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 333 days.

(21) Appl. No.: 10/182,705

(22) PCT Filed: Nov. 26, 2001

(86) PCT No.: PCT/JP01/10272

§ 371 (c)(1),
(2), (4) Date: Aug. 7, 2002

(87) PCT Pub. No.: WO04/48076

PCT Pub. Date: Jun. 20, 2002

(65) Prior Publication Data

US 2003/0023122 A1 Jan. 30, 2003

(30) Foreign Application Priority Data

Dec. 11, 2000 (JP) .......... 2000-375593
Jun. 12, 2001 (JP) .......... 2001-176446

(51) Int. Cl.
*C07C 13/28* (2006.01)

(52) U.S. Cl. .......... 585/21; 585/70; 585/734; 585/750; 585/751; 585/352; 585/360

(58) Field of Classification Search .......... 585/16, 585/20, 734, 750, 751, 352, 21, 360
See application file for complete search history.

(56) References Cited

U.S. PATENT DOCUMENTS 3,671,598 A * 6/1972 Moore .......... 585/350
3,894,098 A * 7/1975 Takaishi et al. .......... 585/352
3,944,626 A 3/1976 Honna et al.

FOREIGN PATENT DOCUMENTS

JP 60-246333 12/1985
JP 4-202143 7/1992

OTHER PUBLICATIONS

Chinese Office Action w/Guo Jianwei et al.; "Synthesis of Adamantane By Using Zeolite Catalyst"; Chinese Journal of Petrochemical Industry, vol. 27, 1998.

* cited by examiner

*Primary Examiner*—Elizabeth D. Wood
(74) *Attorney, Agent, or Firm*—Oblon, Spivak, McClelland, Maier & Neustadt, P.C.

(57) ABSTRACT

It is made possible to efficiently produce adamantane and analogues thereof, namely a hydrocarbon having an adamantane structure by a process which comprises isomerizing a tricyclic saturated hydrocarbon having ten or more carbon atoms in the presence of a solid-acid catalyst containing one or two or more metals selected from among the metals belonging to group VIII in the Periodic Table (group 8 to 12 in the new Periodic Table), wherein one or two or more monocyclic saturated hydrocarbons are added to the tricyclic saturated hydrocarbon having ten or more carbon atoms.

4 Claims, No Drawings

PROCESS FOR PRODUCING ADAMANTANE COMPOUND

TECHNICAL FIELD

The present invention relates to a process for producing a hydrocarbon having an adamantane structure by isomerizing a tricyclic saturated hydrocarbon having ten or more carbon atoms.

BACKGROUND ART

Adamantane is a compound which is obtained by isomerizing, in the presence of a catalyst, trimethylene norbornane (hereinafter sometimes referred to as "TMN") obtainable by hydrogenating dicyclopentadiene (hereinafter sometimes referred to as "DCPD"). In an industrial process for producing the same, aluminum chloride has heretofore been employed as a catalyst. However, in the case of producing adamantane in the presence of aluminum chloride as a catalyst, it is necessary to use a large amount thereof and besides, the catalyst is not reusable because of complex formation with heavy components during the course of reaction. Accordingly, the foregoing process, when being employed therefor, brings about the formation of a large amount of waste aluminum components, whereby the waste treatment thereof gives rise to a problem of environmental pollution. In addition, high corrosiveness of aluminum chloride necessitates the use of an expensive corrosion-resistant materials of construction. Moreover, aluminum chloride, when used therefor, causes the resultant adamantane to be colored and thereby brings about such disadvantages that recrystallizing step and decolorizing step by means of activated carbon or the like are required and hence, a post treatment is made intricate.

On the other hand, a solid-acid catalyst is known which comprises an active metal such as platinum, rhenium, nickel or cobalt each being supported by impregnation method on zeolite that has been subjected to cation exchange by the use of a rare earth metal or an alkaline earth metal {refer to Japanese Patent Publication No. 2909/1977 (Showa 52)}. However, even in the case where the aforesaid solid-acid catalyst is employed, the yield of adamantane is low, unless hydrogen chloride is allowed to coexist therewith, for instance, conversion of TMN of 79.5%, selectivity to adamantane of 10.1% and yield of adamantane of 8.0%. Therefore, hydrogen chloride is indispensable for the isomerization, but high corrosiveness of hydrogen chloride necessitates the use of an expensive corrosion-resistant materials of construction {(refer to Japanese Patent Publication No. 2909/1977 (Showa 52)}.

DISCLOSURE OF THE INVENTION

An object of the present invention is to provide a process for efficiently produce adamantane and analogues thereof by the use of a solid-acid catalyst instead of hydrogen chloride.

As the result of intensive extensive research and investigation made by the present inventors, it has been found that the above-mentioned object is achieved by carrying out the isomerization reaction in the presence of a monocyclic saturated hydrocarbon. Thus the present invention has been accomplished on the basis of the foregoing findings and information.

Specifically, the present invention provides a process for producing adamantane and analogues thereof, namely a hydrocarbon having an adamantane structure which process comprises isomerizing a tricyclic saturated hydrocarbon having ten or more carbon atoms in the presence of a solid-acid catalyst containing one or two or more metals selected from among the metals belonging to group VIII in the Periodic Table (group 8 to 12 in the new Periodic Table), wherein one or two or more monocyclic saturated hydrocarbons are added to the tricyclic saturated hydrocarbon having ten or more carbon atoms.

THE MOST PREFERRED EMBODIMENT TO CARRY OUT THE INVENTION

As mentioned hereinabove, the catalyst to be used in the production process according to the present invention is a solid-acid catalyst containing one or two or more metals selected from among the metals belonging to group VIII in the Periodic Table (group 8 to 12 in the new Periodic Table). The metals belonging to group VIII in the Periodic Table (group 8 to 12 in the new Periodic Table) are not specifically limited. Examples thereof include iron, cobalt, nickel, ruthenium, rhodium, palladium, osmium, iridium and platinum, of which platinum is preferable.

Examples of the solid-acid catalyst to be used in the production process according to the present invention include various types of zeolites (type A, type B, type L, type X, type Y, type ZSM and the like) as typical species, and metal oxides such as silica-alumina, alumina and heteropolyacid. Of these X or Y type zeolite is preferable.

In the following, some description will be given of the case where zeolite is used as the solid-acid catalyst. The catalyst to be used in the production process according to the present invention can be produced by allowing zeolite to be incorporated with one or two or more metals selected from among the metals belonging to group VIII in the Periodic Table (group 8 to 12 in the new Periodic Table) by means of an ion exchange method or an impregnation method.

In the case of an ion exchange method, the catalyst can be produced by bringing any of metals as mentioned above in the state of, for instance, an aqueous solution of a metal salt or a metal complex salt into contact with zeolite so as to subject any of the metals to ion exchange with the cation site (for instance, $H^+$, $NH_4^+$) in the X or Y type zeolite, drying and calcining the zeolite thus ion exchanged. In the case of an impregnation method, the catalyst can be produced by mixing any of the metals in the state of an aqueous solution of a metal salt or a metal complex salt with zeolite, and then evaporating the resultant mixture to dryness by the use of a rotary evaporator or the like so that the metal is impregnated into and supported on the zeolite. The content of the one or two or more metals selected from among the metals belonging to group VIII in the Periodic Table (group 8 to 12 in the new Periodic Table) in the solid-acid catalyst to be used in the production process according to the present invention is not specifically limited, but is preferably at least 0.1% by weight.

The catalyst may be of an optional shape such as powder or granule.

The starting material to be used in the production process according to the present invention is a tricyclic saturated hydrocarbon having ten or more carbon atoms, which is specifically exemplified by trimethylene norbornane (tetrahydrodicyclopentadiene); dimethyltrimethylene norbornane; perhydroacenaphthene; perhydrofluorene; perhydrophenalene; 1,2-cyclopentanoperhydronaphthalene; perhydroanthracene, perhydrophenanthrene; and 9-methylperhydroanthracene. The above-exemplified tricyclic saturated hydrocarbon can be produced by a well-known process, for instance, by the hydrogenation of a corresponding unsaturated hydrocarbon.

In the present invention, the isomerization reaction of the above-mentioned tricyclic saturated hydrocarbon is put into practice in the presence of a monocyclic saturated hydrocarbon, that is, a cycloparaffin. The monocyclic saturated hydrocarbon is preferably a saturated hydrocarbon having 3 to 8 ring members, and may be substituted with a lower alkyl group as the case may be. Preferable monocyclic saturated hydrocarbons are exemplified by cyclopentane, cyclohexane, ethylcyclohexane and methylcyclohexane. Of these are preferable cyclohexane, ethylcyclohexane and the mixture of the above two.

The amount of the monocyclic saturated hydrocarbons to be added to the tricyclic saturated hydrocarbon is not specifically limited, but may be selected according to various circumstances usually in the range of 0.01 to 3 mol, preferably 0.1 to 2 mol per one mol of the tricyclic saturated hydrocarbon.

The isomerization reaction in the production process according to the present invention is carried out in the presence of the above-mentioned catalyst under the conditions including a reaction temperature in the range of 150 to 500° C., preferably 200 to 400° C. and reaction pressure of atmospheric pressure or under pressure. The reaction system may be either continuous system or batchwise system. The reaction is preferably carried out in the presence of hydrogen from the viewpoint of enhancement of adamantane yield.

The amount of the catalyst to be used is 0.01 to 2, preferably 0.05 to 1 in the case of batchwise system.

The regeneration of the catalyst can be carried out by a burning method in air.

In what follows, the present invention will be described in more detail with reference to comparative examples and working examples, which however shall never limit the present invention thereto.

EXAMPLE 1

Na-form Y type zeolite (hereinafter referred to as "NaY") which had a $SiO_2/Al_2O_3$ molar ratio of 5.0 in an amount of 235 g was suspended by stirring in 2000 g of pure water. To the resultant suspension was added 114 g of ammonium sulfate to dissolve in the suspension and thereafter the mixture was heated to 60° C. with stirring for 30 minutes. The resultant slurry was filtered, and then washed by pouring 2500 g of pure water. The washed cake was dried at 110° C. overnight, and calcined in air at 600° C. for 3 hours to obtain a primary ion exchanged product. The resultant primary ion exchanged product was suspended in 2000 g of pure water. To the resultant suspension was added 228 g of ammonium sulfate to dissolve in the suspension and thereafter the mixture was heated to 95° C. with stirring for 30 minutes. Thereafter the suspension was washed with 2000 g of pure water. The foregoing procedure was repeated three times, and the secondary ion exchanged product thus obtained was termed $NH_4$-form Y type zeolite (hereinafter referred to as "$NH_4Y$"). The $NH_4Y$ in an amount of 178 g was placed in a tubular vessel, subjected to steaming at 510° C. for 30 minutes in 100% steam, and suspended by stirring in 2000 g of pure water. To the steamed $NH_4Y$ was added 283 g of 25% sulfuric acid over a period of 30 minutes. Then, the resultant $NH_4Y$ slurry was heated to raise the liquid temperature up to 95° C., subjected to an acid treatment for one hour, filtered followed by washing, and dried at 110° C. overnight to obtain H-form ultrastable Y type zeolite (hereinafter referred to as "HUSY") which had a lattice constant of 24.47 and a $SiO_2/Al_2O_3$ molar ratio as obtained from Breck's formula of 10.4. The HUSY in an amount of 170 g was suspended by stirring in 2000 g of pure water. To the suspension was added 180 g of 1.71% aqueous solution of tetraammineplatinum chloride with stirring at 60° C. for 30 minutes. The resultant mixed suspension was filtered, washed, and dried at 110° C. overnight to obtain a 0.93% Pt/HUSY.

The catalyst in an amount of 4 g which had been obtained through the foregoing procedure was packed in a tubular reactor made of stainless steel (SUS), and was calcined at 300° C. for 3 hours under atmospheric pressure in a stream of air. After the atmosphere in the reactor was replaced with nitrogen, the catalyst was reduced with hydrogen at 300° C. for 3 hours under atmospheric pressure in a stream of hydrogen. Thereafter, supply to the reactor, of mixed solution of TMN and ethylcyclohexane (hereinafter sometimes abbreviated to "ECH") having a TMN:ECH ratio by weight of 1:1 along with hydrogen was commenced so as to proceed with continuous isomerization reaction under the reaction conditions of 250° C., 2 MPa, weight hourly space velocity (WHSV) being 1.2 $h^{-1}$ (on TMN basis) and hydrogen/TMN molar ratio being 2. The reaction results after 40 hours from the start of TMN supply are given in Table 1.

In this connection, conversion of TMN and selectivity to adamantane were each calculated by the following formula, respectively:

Conversion of TMN=(1−weight of TMN after reaction/weight of TMN before reaction)×100

Selectivity to adamantane={weight of formed adamantane/(weight of TMN before reaction−weight of TMN after reaction)}×100

COMPARATIVE EXAMPLE 1

The procedure in Example 1 was repeated to prepare and pretreat a catalyst and proceed with the reaction except that ECH was not added to TMN as the starting material and the reaction was conducted at a WHSV of 2.4 $h^{-1}$ (on TMN basis). The reaction results after 40 hours from the start of TMN supply are given in Table 1.

EXAMPLE 2

NaY which had a $SiO_2/Al_2O_3$ molar ratio of 5.0 in an amount of 235 g was suspended by stirring in 2000 g of pure water. To the resultant suspension was added dilute sulfuric acid to adjust the pH of the suspended slurry to 5.5. Aside therefrom, 246 g of lanthanum nitrate hexahydrate was dissolved in 500 g of warm water. The aqueous solution of lanthanum nitrate thus obtained was gradually mixed with the suspended slurry. Thereafter, the resultant mixture was heated to 90° C., stirred for 30 minutes, then filtered and washed. The washed cake was dried at 110° C. overnight, and calcined at 600° C. for 3 hours.

The powder was again suspended by stirring in 2000 g of pure water, to the resultant slurry was added 228 g of ammonium nitrate, and the mixture was stirred at 95° C. for 30 minutes, filtered and washed. The washed cake was again suspended in 2000 g of pure water, and the suspended slurry was subjected to an ion exchange operation twice consecutively. Subsequently, the resultant ion exchanged product was dried at 110° C. overnight. The dried product was placed in a tubular vessel, subjected to steaming at 510° C. for 30 minutes in 100% steam, and the steamed powder thus obtained was suspended in 2000 g of pure water. The suspended slurry was gradually incorporated with 32 g of 25% sulfuric acid, heated at 95° C. for 30 minutes, then filtered and washed. The washed cake was again suspended in 2000 g of pure water. To the resultant suspension was added 180 g of 1.71% aqueous solution of tetraammine-platinum chloride with stirring at 60° C. for 30 minutes. The resultant mixed suspension was filtered, washed, and dried at 110° C. overnight to obtain a La-containing Y type zeolite on which 0.87% platinum was supported by means of ion exchange (hereinafter sometimes abbreviated to "0.87% Pt/LaUSY").

The catalyst in an amount of 4 g which had been obtained through the foregoing procedure was packed in a tubular reactor made of stainless steel (SUS), and was calcined at 300° C. for 3 hours under atmospheric pressure in a stream of air. After the atmosphere in the reactor was replaced with nitrogen, the catalyst was reduced with hydrogen at 300° C. for 3 hours under atmospheric pressure in a stream of hydrogen. Thereafter, supply to the reactor, of mixed solution of TMN and ethylcyclohexane (hereinafter sometimes abbreviated to "ECH") having a TMN:ECH ratio by weight of 1:1 along with hydrogen was commenced so as to proceed with continuous isomerization reaction under the reaction conditions of 250° C., 2 MPa, weight hourly space velocity (WHSV) being 1.2 $h^{-1}$ (on TMN basis) and hydrogen/TMN molar ratio being 2. The reaction results after 40 hours from the start of TMN supply are given in Table 1.

COMPARATIVE EXAMPLE 2

The procedure in Example 2 was repeated to prepare and pretreat a catalyst and proceed with the reaction except that ECH was not added to TMN as the starting material and the reaction was conducted at a WHSV of 2.4 $h^{-1}$ (on TMN basis). The reaction results after 40 hours from the start of TMN supply are given in Table 1.

EXAMPLE 3

The procedure in Example 2 was repeated to prepare and pretreat a catalyst and proceed with the reaction except that the reaction temperature was set on 300° C. The reaction results after 40 hours from the start of TMN supply are given in Table 1.

EXAMPLE 4

The procedure in Example 3 was repeated to prepare and pretreat a catalyst and proceed with the reaction except that cyclohexane (hereinafter sometimes abbreviated to "CH") was added to TMN in place of ECH. The reaction results after 40 hours from the start of TMN supply are given in Table 1.

COMPARATIVE EXAMPLE 3

The procedure in Comparative Example 2 was repeated to prepare and pretreat a catalyst and proceed with the reaction except that the reaction temperature was set on 300° C. The reaction results after 40 hours from the start of TMN supply are given in Table 1.

EXAMPLE 5

The procedure in Example 2 was repeated to prepare and pretreat a catalyst and proceed with the reaction except that the reaction temperature and reaction pressure were set on 325° C. and 5 MPa, respectively. The reaction results after 40 hours from the start of TMN supply are given in Table 1.

COMPARATIVE EXAMPLE 4

The procedure in Example 5 was repeated to prepare and pretreat a catalyst and proceed with the reaction except that ECH was not added to TMN as the starting material and the reaction was conducted at a WHSV of 2.4 $h^{-1}$ (on TMN basis). The reaction results after 40 hours from the start of TMN supply are given in Table 1.

EXAMPLE 6

The procedure in Example 5 was repeated to prepare and pretreat a catalyst and proceed with the reaction except that the reaction temperature was set on 350° C. The reaction results after 40 hours from the start of TMN supply are given in Table 1.

COMPARATIVE EXAMPLE 5

The procedure in Example 6 was repeated to prepare and pretreat a catalyst and proceed with the reaction except that ECH was not added to TMN as the starting material and the reaction was conducted at a WHSV of 2.4 $h^{-1}$ (on TMN basis). The reaction results after 40 hours from the start of TMN supply are given in Table 1.

TABLE 1

| | Catalyst | Additive | Reaction temperature (° C.) | Reaction pressure (MPa) | Conversion of TMN (% by weight) | Selectivity To adamantane (% by weight) |
|---|---|---|---|---|---|---|
| Example 1 | Pt/HUSY | ECH | 250 | 2 | 99.7 | 10.0 |
| Comparative Example 1 | " | None | " | " | 46.4 | 10.0 |
| Example 2 | Pt/LaUSY | ECH | " | " | 91.8 | 15.1 |
| Comparative Example 2 | " | None | " | " | 37.1 | 13.0 |
| Example 3 | " | ECH | 300 | " | 43.4 | 21.5 |
| Example 4 | " | CH | " | " | 17.8 | 30.2 |
| Comparative Example 3 | " | None | " | " | 21.6 | 15.5 |
| Example 5 | " | ECH | 325 | 5 | 99.5 | 15.5 |
| Comparative Example 4 | " | None | " | " | 91.2 | 15.3 |
| Example 6 | " | ECH | 350 | " | 99.7 | 13.2 |
| Comparative Example 5 | " | None | " | " | 95.2 | 12.8 |

As can be clearly seen from Table 1, the use of ECH leads to marked enhancement of the conversion of TMN, while the use of CH leads to marked enhancement of the selectivity to adamantane.

INDUSTRIAL APPLICABILITY

By carrying out the isomerization reaction of a tricyclic saturated hydrocarbon in the presence of a monocyclic saturated hydrocarbon according to the present invention, it is made possible to markedly enhance the conversion of the tricyclic saturated hydrocarbon as the starting material as well as the selectivity to adamantane. In addition, since no use is made of a highly corrosive substance such as hydrogen chloride at the time of production, it is made possible to efficiently produce adamantane and analogues thereof at a low cost, dispensing with the use of a corrosion resistant material in production equipment.

What is claimed is:

1. A process for producing adamantane and analogues thereof, namely a hydrocarbon having an adamantane structure which process comprises isomerizing a tricyclic saturated hydrocarbon having ten or more carbon atoms in the presence of a solid-acid catalyst containing one or two or more metals selected from among the metals belonging to group VIII in the Periodic Table (group 8 to 12 in the new Periodic Table), characterized in that one or two or more monocyclic saturated hydrocarbons are added to the tricyclic saturated hydrocarbon having ten or more carbon atoms.

2. The process for producing adamantane and analogues thereof according to claim 1, wherein the monocyclic saturated hydrocarbon is cyclohexane, ethylcyclohexane or a mixture thereof.

3. The process for producing adamantane and analogues thereof according to claim 1, wherein the metal belonging to group VIII in the Periodic Table (group 8 to 12 in the new Periodic Table) is platinum.

4. The process for producing adamantane and analogues thereof according to claim 1, wherein the solid-acid catalyst is Y type zeolite.

* * * * *

UNITED STATES PATENT AND TRADEMARK OFFICE
CERTIFICATE OF CORRECTION

PATENT NO. : 7,019,183 B2
DATED : March 28, 2006
INVENTOR(S) : Kojima et al.

It is certified that error appears in the above-identified patent and that said Letters Patent is hereby corrected as shown below:

<u>Title page,</u>
Item [87], should read:
-- [87]  PCT Pub. No.: WO02/48076
         PCT Pub. Date: Jun. 20, 2002 --.

Signed and Sealed this

Thirteenth Day of June, 2006

JON W. DUDAS
*Director of the United States Patent and Trademark Office*